(12) United States Patent
Rewinkel et al.

(10) Patent No.: US 7,989,442 B2
(45) Date of Patent: Aug. 2, 2011

(54) PROGESTERONE RECEPTOR MODULATORS

(75) Inventors: Johannes Bernardus Maria Rewinkel, Oss (NL); Brigitte Johanna Bernita Folmer, Oss (NL); Maria Lourdes Ollero, Oss (NL); Hemen Ibrahim, Oss (NL)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/861,427

(22) Filed: Sep. 26, 2007

(65) Prior Publication Data

US 2008/0090804 A1    Apr. 17, 2008

Related U.S. Application Data

(60) Provisional application No. 60/847,605, filed on Sep. 27, 2006.

(51) Int. Cl.
*A61P 5/24* (2006.01)
*A61P 35/00* (2006.01)
*A61K 31/55* (2006.01)
*C07D 471/04* (2006.01)
*C07D 498/04* (2006.01)
*C07D 513/04* (2006.01)

(52) U.S. Cl. .................................. 514/211.09; 540/546

(58) Field of Classification Search ............. 514/211.09; 540/546
See application file for complete search history.

(56) References Cited

U.S. PATENT DOCUMENTS 5,688,810 A    11/1997    Jones et al.

FOREIGN PATENT DOCUMENTS

| EP | 0 303 306 | 3/1993 |
|----|-----------|--------|
| EP | 0 876 815 | 4/1998 |
| WO | WO 03/084963 | 10/2003 |

*Primary Examiner* — Brenda Coleman
(74) *Attorney, Agent, or Firm* — Patricia Chisholm; Susan Hess

(57) ABSTRACT

The present invention provides new progesterone receptor modulators which are (cis)-8-fluorodibenzo[b,f]pyrido[1,2-d]oxazepine-1-amine compounds and uses thereof.

30 Claims, No Drawings

PROGESTERONE RECEPTOR MODULATORS

This application claims benefit of provisional application No. 60/847,605 filed Sep. 27, 2006.

The present invention relates to (cis)-8-fluorodibenzo[b,f]pyrido[1,2-d]oxazepine-1-amine derivatives that are modulators of progesterone receptors, to their application in the field of contraception, hormone replacement therapy (HRT) or therapy of gynaecological disorders, as well as adjuvant therapy in cancer and other diseases, and to methods for the making and use of such compounds.

Intracellular receptors are a class of structurally related proteins involved in the regulation of gene transcription. Steroid receptors are a subset of these receptors, including the progesterone receptor (PR), androgen receptor (AR), estrogen receptor (ER), glucocorticoid receptor (GR) and mineralocorticoid receptor (MR). Regulation of a gene requires the intracellular receptor and a corresponding ligand which has the ability to selectively bind to the receptor in a way that affects gene transcription.

Progesterone receptor modulators (progestagens and antiprogestagens) are known to play an important role in the health of women. The natural ligand for PR is the steroid hormone progesterone, but synthetic compounds have been made which may also serve as ligands (see e.g. Jones et al., U.S. Pat. No. 5,688,810).

Progestagens are currently widely used for hormonal contraception and in HRT. Other important clinical applications of progestagens are treatment of gynaecological disorders (e.g. endometriosis, dysmenorrhea, dysfunctional uterine bleeding, severe premenstrual syndrome), breast cancer, hot flushes and mood disorders, and luteal support during IVF. In addition, they are applied in combination with other hormones and/or other therapies including, without limitation, chemotherapeutic agents such as cytotoxic and cytostatic agents, immunological modifiers such as interferons and interleukins, growth hormones or other cytokines, hormone therapies, surgery and radiation therapy.

The current steroidal progestagens have been proven to be quite safe and are well tolerated. Sometimes, however, side effects (e.g. breast tenderness, headaches, depression, and weight gain) have been reported that are attributed to these steroidal progestagens, either alone or in combination with estrogenic compounds. In addition, steroidal ligands for one receptor often show cross-reactivity with other steroidal receptors. Many steroidal progestagens also bind e.g. to the androgen receptor, whereas many antiprogestagens have affinity for the glucocorticoid receptor.

Non-steroidal progestagens have no structural similarity with steroids and therefore might be expected to display differential behaviour with respect to physicochemical properties, pharmacokinetic (PK) parameters, or tissue distribution (e.g. CNS versus peripheral), and, more importantly, may show no or less cross-reactivity to other steroid receptors. Therefore, non-steroidal progestagens may be expected to score differently on these aspects and thus offer advantages over steroidal progestagens when applied in therapy.

A group of non-steroidal molecules which contain a 1,3,4,14b-tetrahydro-2H-dibenzo[b,f]pyrido[1,2-d]oxazepine system as a core, have been described as non-steroidal progesterone receptor modulators with affinity for the progesterone receptor (WO 03/084963). The compounds disclosed therein show a moderate to strong agonistic activity in vitro towards the progesterone receptor. The most active compounds showed an affinity of 10 nM or less. In addition, some of the compounds from WO 03/084963 showed a weak to moderate antiprogestagenic activity in vitro.

The compounds of the present invention show similar agonistic activity in vitro as the compounds from WO 03/084963. Surprisingly however, the particular combination of specific substituents, more specifically a nitrile substituent in position 7 in combination with a fluoro substituent in position 8, gives rise to a much enhanced progestagenic activity in vivo, as indicated by the results of the ovulation inhibition assay. This gives the compounds of the present invention an advantage over known compounds having a similar structure: as is recognized by those skilled in the art, a high in vivo activity in a test assay is highly indicative of a strong activity upon application in therapy, especially in human subjects. Moreover, skilled artisans will recognize that when the in vivo assay uses oral administration, a high activity (i.e., an activity which can be achieved by administering relatively low amounts of compound) is a desirable property for compounds which in therapy may e.g. be administered by the oral route.

The present invention thus provides compounds which exert a strong progestagenic effect in vivo. More particularly, the present invention relates to (cis)-8-fluorodibenzo[b,f]pyrido[1,2-d]oxazepine-1-amine compounds and compositions which are high-affinity progesterone agonists which also show a remarkably high in vivo progestagenic potency.

According to the present invention, (cis)-8-fluorodibenzo[b,f]pyrido[1,2-d]oxazepine-1-amine compounds are provided having general Formula I.

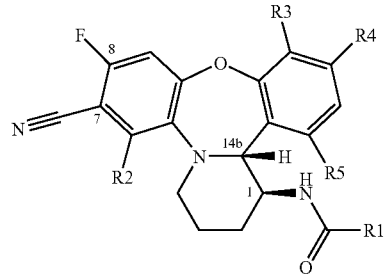

Formula I wherein
R1 is (1-4C)alkyl, optionally substituted with one or more halogen atoms; and
R2 is selected from the group consisting of H, halogen, (1-6C)alkyl, and CN; and
R3, R4 and R5 each are independently H or F.

In a specific embodiment R1 is $CF_3$. In another embodiment, R1 is $CH_3$.

In one embodiment, R2 is H. In another embodiment, R2 is Cl and in yet another embodiment R2 is CN.

In one embodiment, R3 is H, in another embodiment R3 is F.

In one embodiment, R4 is H, in another embodiment R4 is F.

In one embodiment, R5 is H, in another embodiment R5 is F.

In one embodiment, R3, R4 and R5 are H. In another embodiment, R3 is F and both R4 and R5 are H. In another embodiment, R4 is F and both R3 and R5 are H and in yet another embodiment R5 is F and both R3 and R4 are H.

In a specific embodiment, R1 is $CF_3$, R2 is H, R3 is H, R4 is H and R5 is H.

In another specific embodiment, R1 is $CF_3$, R2 is Cl, R3 is H, R4 is H and R5 is H.

In addition, the present invention provides compounds useful as intermediates or precursors in preparing the compounds of Formula I where R1, R3, R4 and R5 have the meaning given previously and where R2 is H. These (cis)-8-fluorodibenzo[b,f]pyrido[1,2-d]oxazepine-1-amine compounds have general Formula II wherein R1 is (1-4C)alkyl, optionally substituted with one or more halogen atoms.

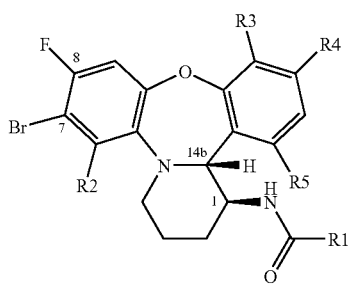

Formula II

It should be noted that both in Formula I and in Formula II the amino substituent at position 1 and the bridgehead hydrogen substituent at position 14b are located on the same side of the ring system. This relative stereochemistry, that is the stereochemistry where the absolute orientation of one substituent is linked to the absolute orientation of another substituent, is reflected in the nomenclature of the compounds by the use of the prefix (cis)-.

The compounds of the subject invention are envisaged for use in therapy.

The subject invention provides a contraceptive composition comprising a compound of the subject invention and a contraceptively acceptable carrier. The subject invention also provides a pharmaceutical composition comprising a compound of the subject invention and a pharmaceutically acceptable carrier. In one embodiment, a pharmaceutical composition is envisaged for hormone replacement therapy. In another embodiment, a pharmaceutical composition is envisaged for the treatment of a gynaecological disorder.

The subject invention furthermore involves a use of a compound of the subject invention for the manufacture of a contraceptive. The subject invention also envisages a use of a compound of the subject invention for the manufacture of a medicament. In one embodiment, a use of a compound of the subject invention is for the manufacture of a medicament for hormone replacement therapy, or, in another embodiment, for the treatment of a gynaecological disorder.

The subject invention furthermore provides a method of contraception comprising administering a contraceptively effective amount of a compound of the subject invention to an individual in need thereof.

The subject invention furthermore provides a method of providing hormone replacement therapy comprising administering a pharmaceutically effective amount of a compound of the subject invention to an individual in need thereof.

The subject invention furthermore provides a method of treating a gynaecological disorder comprising administering a pharmaceutically effective amount of a compound of the subject invention to an individual in need thereof.

Furthermore, the subject invention provides a compound of Formula II useful in the manufacture of a compound of Formula I, in that compounds of Formula II serve as intermediate in the preparation of compounds of Formula I. As depicted in Scheme 1 these intermediates of Formula II can be converted to compounds of Formula I by use of CuCN, optionally in the presence of CuI.

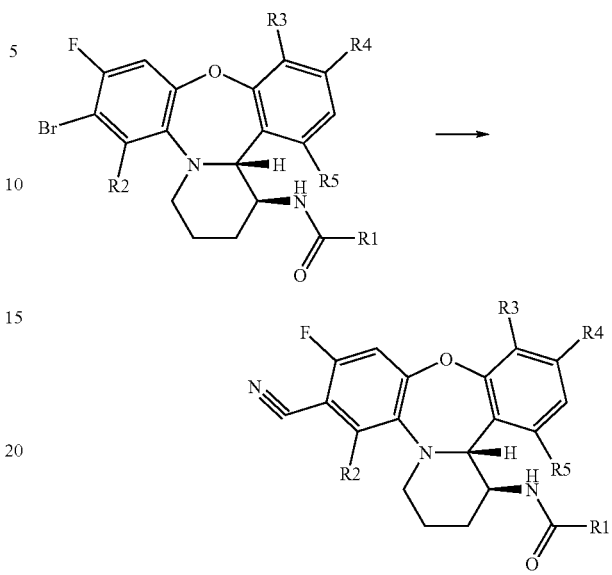

Scheme 1

Compounds of Formula II can be prepared as described in WO 03/084963. Optionally, several compounds of Formula I in which R2 has the meaning given above except that R2 is not hydrogen, can be prepared from compounds of Formula II. The latter compounds can be chlorinated using N-chlorosuccinimide or other chlorinating reagents known in the art, yielding compounds of Formula I in which R2=Cl. These chloro compounds can be transformed in compounds of Formula I in which R2=(another) halogen, (1-6C)alkyl or CN using various reactions known in the art (Scheme 2).

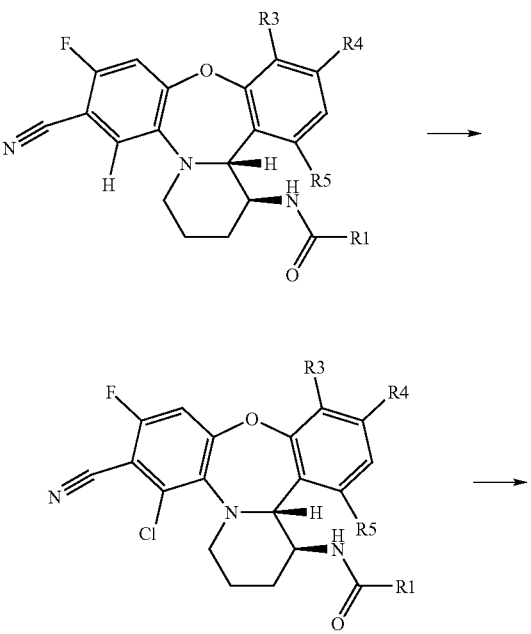

Scheme 2

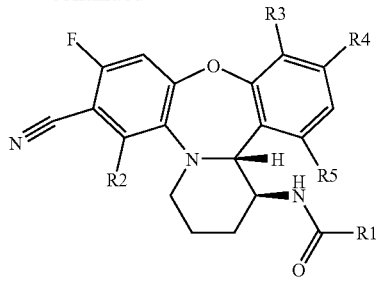

Racemates of compounds of Formula I or of Formula II can be separated into their enantiomers using various methods known in the art, one such method being the use of chromatography on chiral columns.

Another suitable method of resolution is the use of optically pure acids such as tartaric acid or Phencyphos to prepare diastereomerically pure salts of amines of Formula III in which R2 has the meaning as in Formula I. Methods to prepare amines of Formula III and the use of these amines to prepare amides of Formula II are described in WO 03/084963.

Formula III

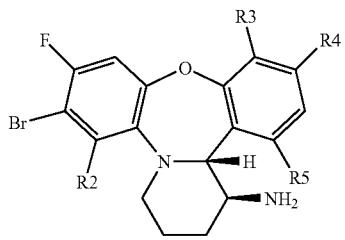

The terms used in this description have the following meaning:
(1-4C)alkyl is a branched or unbranched alkyl group having 1, 2, 3 or 4 C atoms, for example methyl, ethyl, propyl, isopropyl, butyl, sec-butyl, tert-butyl, and the like;
(1-6C)alkyl is a branched or unbranched alkyl group having 1, 2, 3, 4, 5, or 6 C atoms, for example methyl, ethyl, propyl, isopropyl, butyl, sec-butyl, tert-butyl, pentyl, sec-pentyl, iso-pentyl, hexyl, sec-hexyl, iso-hexyl and the like;
Halogen refers to fluorine, chlorine, bromine or iodine;

For the purposes of the present invention, and according to the practices of Chemical Abstracts Service (see Naming and Indexing of Chemical Substances for CHEMICAL ABSTRACTS, the American Chemical Society, Columbus, Ohio 1987) the indication (cis) when naming fused polycyclic compounds such as those of the present invention shall be understood to mean the relative stereochemistry where the ring substituent in position 1 (Formula I) is located on the same side of said ring as the bridgehead substituent (which in Formula I is hydrogen) in position 14b. The meaning of the term (cis) will furthermore be clear to those skilled in the art from the illustrations in the various Figures, Diagrams and Reaction Schemes.

A racemate is a mixture of equal parts of enantiomers; as will be known to those skilled in the art, a racemate, also called racemic mixture or racemic preparation, is optically inactive since the optical activities of the dextrorotatory and laevorotatory enantiomers cancel out. Also see R. T. Morrison and R. N. Boyd, Organic Chemistry (3rd Ed). Allyn & Bacon, Boston, 1973, p 127.

An enantiomer is called laevorotatory when it is found, upon determination of its optical activity, to produce a counter-clockwise rotation of the plane of polarized light. Likewise, a compound is called dextrorotatory if said rotation of the plane of polarized light is clockwise (Also see R. T. Morrison and R. N. Boyd, Organic Chemistry (3rd Ed). Allyn & Bacon, Boston, 1973, p 119). As will be known to those skilled in the art, however, the sign ('+' or 'plus' for dextrorotatory and '−' or 'minus' for laevorotatory) of the rotation of the plane of polarized light is dependent on the temperature, the wavelength of the polarized light, and (when the rotation of a compound is determined in solution) the concentration and the solvent (also see J. March, Advanced Organic Chemistry 2nd Ed. McGraw-Hill Kogakusha, Tokyo 1977 p 87 ff).

The progestagen receptor affinity and efficacy of the compounds according to the invention make them suitable for use in control of fertility and reproduction, e.g. in female contraception, and further for female HRT, the treatment of gynaecological disorders, as components of male contraception and in diagnostic methods focussed on the amount and/or location of progesterone receptors in various tissues. For the latter purpose it can be preferred to make isotopically labelled variants of the compounds according to the invention.

The compounds of the invention may further be useful for the treatment of endometriosis, menorrhagia, menometrorrhagia, dysmenorrhoea, acne, fibroids, osteoporosis as well as other bone disorders, bone fraction repair, sarcopenia, frailty, skin ageing, female sexual dysfunction, postmenopausal symptoms, atherosclerosis, aplastic anaemia, lipodystrophy, side effects of chemotherapy, tumours (located in e.g. breast, ovary and uterus) and others.

Suitable routes of administration for the compounds of the subject invention (also called active ingredient) are oral, rectal, nasal, topical (including transdermal, buccal and sublingual), vaginal or parenteral (including subcutaneous, intramuscular, intravenous and intradermal) administration or administration via an implant. In a specific embodiment, the compounds can be administered orally.

The exact dose and regimen of administration of the active ingredient, or a contraceptive or pharmaceutical composition thereof, will necessarily be dependent upon the therapeutic effect to be achieved (e.g. contraception, HRT) and may vary with the particular compound, the route of administration, and the age and condition of the individual subject to whom the medicament is to be administered.

A dosage for humans is likely to contain 0.0001-25 mg per kg body weight. The desired dose may be presented as one dose or as multiple sub-doses administered at appropriate intervals.

The present invention thus also relates to contraceptive and pharmaceutical compositions comprising a compound according to Formula I in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy, for example, using methods such as those described in Gennaro et al., Remington's Pharmaceutical Sciences (18th ed., Mack Publishing company, 1990, see especially Part 8: *Pharmaceutical Preparations and Their Manufacture*).

Such methods include the step of bringing in association the active ingredient with any auxiliary agent. The auxiliary agent(s), also named accessory ingredient(s), include those conventional in the art (Gennaro, supra), such as carriers, fillers, binders, diluents, disintegrants, lubricants, colorants, flavouring agents, anti-oxidants, and wetting agents.

Pharmaceutical and contraceptive compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a contraceptive and a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The compounds of the invention can also be administered in the form of devices consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in EP 303306.

The compounds of the invention can also be administered in the form of a vaginal ring such as described for example in EP 876815.

The compounds of the invention may be administered in conjunction with estrogens, androgens, progestagens, anti-progestagens, and other suitable compounds such as folic acid, vitamins, minerals etc.

EXAMPLES

The invention is further described in the following examples, which are not in any way intended to limit the scope of the inventions as claimed.

In the examples the following abbreviations are used:
$CH_2Cl_2$: dichloromethane
CuBr: copper (I) bromide
CuCN: copper (I) cyanide
CuI: copper (I) iodide
DMSO: dimethyl sulfoxide
DPPA: diphenylphosphoryl azide
e.e.: enantiomeric excess
$K_2CO_3$: potassium carbonate
M: molar
$MgSO_4$: magnesium sulfate
$NaHCO_3$: sodium hydrogencarbonate
NaOH: sodium hydroxide
$Na_2SO_4$: sodium sulfate
NCS: N-chlorosuccinimide
$NH_4OH$: ammonium hydroxide
NMP: N-methylpyrrolidone
NMR: nuclear magnetic resonance
P.S. filter: Phase Separation filter
$SiO_2$: silicon dioxide (silica gel)
THF: tetrahydrofuran Example 1

Preparation of (−)-(cis)-N-(7-bromo-8-fluoro-1,3,4,14b-tetrahydro-2H-dibenzo [b,f]pyrido[1,2-d][1,4]oxazepin-1-yl)-2,2,2-trifluoroacetamide (Formula II, R1=$CF_3$, R2=R3=R4=R5=H)

a. 2-[[(5-bromo-2,4-difluorophenyl)imino]methyl]phenol

A solution of 2,4-difluoro-6-bromoaniline (5 g, 24 mmol), salicylaldehyde (2.5 mL, 24 mmol) and p-toluenesulfonic acid (14 mg, 0.07 mmol) in toluene (120 mL) was heated to reflux in a Dean-Stark apparatus for 2.5 h and then allowed to cool to ambient temperature. After adding triethylamine (1 mL) the reaction mixture was concentrated to give the crude title compound (7.3 g, 97%) which was used without further purification. $^1$H-NMR (400 MHz, $CDCl_3$) 6.95-6.99 (m, 1H), 7.01-7.06 (m, 2H), 7.39-7.45 (m, 2H), 7.48-7.52 (m, 1H), 8.66 (s, 1H), 12.69 (s, 1H). (m/z)=312+314 $(M+H)^+$.

b. 8-bromo-7-fluorodibenz[b,f][1,4]oxazepine

To a solution of 2-[[(5-bromo-2,4-difluorophenyl)imino]methyl]phenol (14.5 g, 46.5 mmol) in DMSO (0.43 L), $K_2CO_3$ (12.8 g, 71.8 mmol) and 18-Crown-6 (145 mg, 0.55 mmol) were added. The resulting mixture was stirred at 140° C. for 2.5 h and then allowed to cool to ambient temperature. Water (0.6 L) was added and the product was collected by filtration, washed with water and dried under reduced pressure to yield the title compound (15.7 g, 100%) which was used without further purification. $^1$H-NMR (400 MHz, $CDCl_3$) 6.93-6.96 (d, J=8.2, 1H), 7.10-7.14 (d, J=8.2, 1H), 7.23-7.28 (m, 1H), 7.34-7.37 (m, 1H), 7.46-7.51 (m, 1H), 7.55-7.57 (d, J=7.8, 1H), 8.47 (s, 1H). (m/z)=292+294 $(M+H)^-$.

c. (±)-(cis)-7-bromo-8-fluoro-1,3,4,14b-tetrahydro-4-oxo-2H-dibenzo[b,f]pyrido[1,2-d] [1,4]oxazepine-1-carboxylic acid Glutaric anhydride (7.2 g, 63 mmol) was added to a stirred solution of 8-bromo-7-fluoro-dibenz[b,f][1,4]oxazepine (46.5 mmol) in xylene (26 mL) and the mixture was heated to 140° C. for 120 h. The reaction mixture was allowed to cool to ambient temperature, ether was added and the solution extracted (3×) with 2M NaOH. The pH of the combined extracts was adjusted to pH 4 by adding 3M hydrochloric acid. The product was collected by filtration and dried to yield the title compound (14.1 g, 81%) which was used without further purification. $^1$H-NMR (400 MHz, $CDCl_3$) 2.03-2.14 (m, 1H), 2.31-2.4 (m, 1H), 2.53-2.62 (m, 1H), 2.67-2.81 (m, 1H), 3.55-3.60 (m, 1H), 5.46-5.49 (m, 1H), 7.05-7.09 (d, J=8.6, 1H), 7.11-7.32 (m, 4H), 7.56-7.59 (d, J=7.8, 1H). (m/z)=406+408 $(M+H)^+$.

d. Methyl (±)-(cis)-(7-bromo-8-fluoro-1,3,4,14b-tetrahydro-4-oxo-2H-dibenzo [b,f]pyrido[1,2-d][1,4]oxazepin-1-yl)carbamate To a solution of (±)-(cis)-7-bromo-8-fluoro-1,3,4,14b-tetrahydro-4-oxo-2H-dibenzo[b,f]pyrido[1,2-d][1,4]oxazepine-1-carboxylic acid (13.1 g, 32.3 mmol) in toluene (660 mL), triethylamine (7.6 mL, 54 mmol) and diphenyl phosphorazidate (9.1 mL, 42 mmol) were added. The reaction mixture was heated to reflux for 2 h. Subsequently, methanol (31.9 mL, 787 mmol) was added and stirring was continued for 2 h at 70° C. After cooling down to room temperature, the reaction mixture was dried over P.S. filter and evaporated, to give the crude title compound (30.5 g, 100%) which was used without further purification. (m/z)=435+437 (M+H)$^-$.

e. Methyl (±)-(cis)-(7-bromo-8-fluoro-1,3,4,14b-tetrahydro-2H-dibenzo[b,f]pyrido[1,2-d][1,4]oxazepin-1-yl)carbamate Borane-tetrahydofuran complex (1.0 M in THF, 970 mL, 970 mmol) was added dropwise to a stirred solution of methyl (±)-(cis)-(7-bromo-8-fluoro-1,3,4,14b-tetrahydro-4-oxo-2H-dibenzo[b,f]pyrido[1,2-d][1,4]oxazepin-1-yl)carbamate (105.2 g, 242 mmol) in THF (1 L). The resulting mixture was stirred at ambient temperature for 3 h. Subsequently, hydrochloric acid (1M) was added dropwise until evolution of gas ceased (±550 mL). The resulting mixture was stirred for 1 h and then diluted with ethyl acetate; the organic layer was washed with water and brine. After drying (MgSO$_4$) the solvent was evaporated under reduced pressure to yield the crude title compound (98.5 g, 97%). (m/z)=421+423 (M+H)$^+$.

f. (±)-(cis)-7-bromo-8-fluoro-1,3,4,14b-tetrahydro-2H-dibenzo[b,f]pyrido[1,2-d][1,4]oxazepin-1-amine A mixture of acetic acid (40 mL) and hydrogen bromide (48%, 20 mL) was added to methyl (±)-(cis)-(7-bromo-8-fluoro-1,3,4,14b-tetrahydro-2H-dibenzo[b,f]pyrido[1,2-d][1,4]oxazepin-1-yl)carbamate (20.2 g, 48 mmol) and stirred overnight at 100° C. After cooling down the reaction mixture was poured into a cold 1M NaOH solution. It was extracted with CH$_2$Cl$_2$ and the organic layer was washed with brine, dried (MgSO$_4$) and the solvent was evaporated under reduced pressure to yield the crude title compound (15.9 g, 91%) which was used without further purification. (m/z)=363+365 (M+H)$^+$.

g. (−)-(cis)-7-bromo-8-fluoro-1,3,4,14b-tetrahydro-2H-dibenzo[b,f]pyrido[1,2-d][1,4]oxazepin-1-amine (4S)-2-hydroxy-5,5-dimethyl-4-phenyl-1,3,2-dioxaphosphorinane 2-oxide (1:1)

To a solution of (±)-(cis)-7-bromo-8-fluoro-1,3,4,14b-tetrahydro-2H-dibenzo[b,f]pyrido[1,2-d][1,4]oxazepin-1-amine (18.58 g, 51.18 mmol) in 300 mL of CH$_2$Cl$_2$ and 60 mL of 2-propanol at 50° C. was added a warm solution of (+)-phencyphos (6.19, 25.59 mmol) in CH$_2$Cl$_2$ (300 mL) and 2-propanol (75 mL). The mixture was heated at 86° C. About 500 mL of CH$_2$Cl$_2$ was removed by careful evaporation, and 310 mL of 2-propanol was added; the mixture was then further concentrated until a final weight of ca. 250 g, and then gradually cooled down to 35° C. After 1 h, the formed crystals were collected by filtration, washed with 2-propanol and dried to yield 12.7 g of crude product (e.e. =95%). This compound was further recrystallized from methanol:CH$_2$Cl$_2$:2-propanol (7:5:2) to give the title compound (12.3 g, 39%, e.e.=99.8%).

h. (−)-(cis)-7-bromo-8-fluoro-1,3,4,14b-tetrahydro-2H-dibenzo[b,f]pyrido[1,2-d][1,4]oxazepin-1-amine 1M NaOH (580 ml, 580 mmol) was added to a solution of (−)-(cis)-7-bromo-8-fluoro-1,3,4,14b-tetrahydro-2H-dibenzo[b,f]pyrido[1,2-d][1,4]oxazepin-1-amine (4S)-2-hydroxy-5,5-dimethyl-4-phenyl-1,3,2-dioxaphosphorinane 2-oxide (1:1) (45,42 g 75 mmol) in 1L of ethanol:CH$_2$Cl$_2$ (1:9), and the resulting biphasic mixture was vigorously stirred at ambient temperature for 0.5 h. The aqueous layer was extracted with CH$_2$Cl$_2$ (400 mL) and the combined organic layers were washed with 0.4M NaOH, dried (Na$_2$SO$_4$) and evaporated under reduced pressure to yield the title compound (27.2 g, 100%). $^1$H-NMR (400 MHz, CDCl$_3$) 1.40-1.51 (m, 1H), 1.69-1.89 (m, 2H), 2.14-2.22 (m, 1H), 3,11-3.29 (m, 1H), 3.38-3.45 (m, 1H), 3.68-3.76 (m, 2H), 6.87-6.90 (d, J=8.0, 1H), 7.03-7.30 (m, 5H). $^{19}$F-NMR (400 MHz, CDCl$_3$) −118.27. (m/z)=363+365 (M+H)$^+$. (e.e. =99.9%) (chiralpak AD-H 25*0.46 cm, heptane:ethanol=8:2). (m/z)=363+365 (M+H)$^+$. $[\alpha]_D^{20.5}$=−202° (c=1.0, CHCl$_3$)

i. (−)-(cis)-N-(7-bromo-8-fluoro-1,3,4,14b-tetrahydro-2H-dibenzo[b,f]pyrido[1,2-d][1,4]oxazepin-1-yl)-2,2,2-trifluoroacetamide To a solution of (−)-(cis)-7-bromo-8-fluoro-1,3,4,14b-tetrahydro-2H-dibenzo[b,f]pyrido[1,2-d][1,4]oxazepin-1-amine (27.51 g, 75.78 mmol) in a mixture of CH$_2$Cl$_2$ (866 mL) and pyridine (33.56 mL), trifluoroacetic anhydride (33.84 mL, 242 mmol) was added and the resulting mixture was stirred at ambient temperature for 1.5 h. The crystals formed were collected by filtration, washed with CH$_2$Cl$_2$ and with water, and dried under reduced pressure to yield the title compound (−)-(cis)-N-(7-bromo-8-fluoro-1,3,4,14b-tetrahydro-2H-dibenzo[b,f]pyrido[1,2-d][1,4]oxazepin-1-yl)-2,2,2-trifluoroacetamide (31.36 g, 90%). $^1$H-NMR (400 MHz, DMSO) 1.60-1.85 (m, 3H), 1.97-2.04 (m, 1H), 3.07-3.16 (m, 1H), 3.73-3.80 (d, J=12.9, 1H), 4.07-4.10 (d, J=9.7, 1H), 4.31-4.42 (m, 1H), 7.04-7.09 (m, 1H), 7.15-7.21 (m, 2H), 7.24-7.33 (m, 3H), 9.18-9.21 (d, J=9.7, 1H). (m/z)=459+461 (M+H)$^+$. $[\alpha]_D^{20}$=−197° (c=1.0055, THF).

Example 2

Preparation of (−)-(cis)-N-(7-cyano-8-fluoro-1,3,4,14b-tetrahydro-2H-dibenzo[b,f]pyrido[1,2-d][1,4]oxazepin-1-yl)-2,2,2-trifluoroacetamide (Formula I, R1=CF$_3$, R2=R3=R4=R5=H)

A mixture of (−)-(cis)-N-(7-bromo-8-fluoro-1,3,4,14b-tetrahydro-2H-dibenzo[b,f]pyrido[1,2-d][1,4]oxazepin-1-yl)-2,2,2-trifluoroacetamide (17 g, 37 mmol), CuCN (8.19, 91.5 mmol), CuI (0.754 g, 3.9 mmol) and NMP (178 mL) was stirred for 20 min. at 180° C., 300 Watt with cooling in microwave (in 5 portions). After cooling down, the reaction mixture was poured into water, diluted with NH$_4$OH-solution and extracted with ethyl acetate. The organic layer was washed with water, brine, dried (Na$_2$SO$_4$) and concentrated under reduced pressure. The white solid that remained was washed with diethyl ether and crystallized to give the title compound (8.1 g, 54%). $^1$H-NMR (400 MHz, DMSO) 1.66 (m, 1H), 1.74 (m, 1H), 1.82 (m, 1H), 2.01 (m, 1H), 3.16 (m, 1H), 3.85 (m, 1H), 4.14 (d, J=10.01, 1H), 4.39 (m, 1H), 7.10 (td, J=7.74, 7.3 and 1.32 Hz, 1H), 7.20 (dd, J=7.74 and 1.70 Hz, 1H), 7.23 (dd, J=7.93 and 1.32 Hz, 1H), 7.29 (td, J=7.93, 7.37 and 1.32 Hz, 1H), 7.42 (d, J=9.44, 1H), 7.57 (d, J=6.42, 1H), 9.21 (d, J=10.01, 1H). $^{19}$F-NMR (400 MHz, DMSO) -119.08 (Ar—F), −74.96 (COCF$_3$). e.e.=100%. (chiralpak AD-H 25*0.46 cm, heptane:isopropanol=9:1). (m/z)=405 (M+H)$^+$. $[\alpha]_D^{20.5}$=−214° (c=1.03, THF).

Example 3

Preparation of (−)-(cis)-N-[6-chloro-7-cyano-8-fluoro-1,3,4,14b-tetrahydro-2H-dibenzo [b,f]pyrido [1,2-d][1,4]oxazepin-1-yl]-2,2,2-trifluoroacetamide (Formula I, R1=CF$_3$, R2=Cl, R3=R4=R5=H)

To a suspension of (−)-(cis)-N-[7-cyano-8-fluoro-1,3,4,14b-tetrahydro-2H-dibenzo[b,f]pyrido[1,2-d][1,4]oxazepin-1-yl]-2,2,2-trifluoroacetamide (17.1 g, 42.2 mmol) in THF were added NCS (6.16 g, 46.4 mmol) and hydrochloric acid (7.8 mL, 46.4 mmol) and the resulting mixture was stirred at ambient temperature for 2.5 h. The reaction mixture was then poured into water and extracted with ethyl acetate (2×). The combined organic layers were washed with sat. NaHCO$_3$ (aq) and with brine, dried (Na$_2$SO$_4$) and evaporated to afford the crude compound which was purified by flash chromatography (SiO$_2$, ethyl acetate/heptane) to give (−)-(cis)-N-(6-chloro-7-cyano-8-fluoro-1,3,4,14b-tetrahydro-2H-dibenzo [b,f]pyrido[1,2-][1,4]oxazepin-1-yl)-2,2,2-trifluoroacetamide (16.1 g, 78%). $^1$H-NMR (400 MHz, CDCl$_3$) 1.64 (m, 1H), 1.91 (m, 1H), 1.94 (m, 1H), 2.02 (m, 1H), 2.88 (m, 1H), 3.05 (m, 1H), 4.44 (d, J=1.55 Hz, 1H), 4.91 (m, 1H), 6.97 (d, J=9.44 Hz 1H), 7.19-7.40 (m, 4H), 7.66-7.74 (d, J=8.2 Hz, 1H). $^{19}$F-NMR (400 MHz, CDCl$_3$) −105.82 (Ar—F), −76.33 (COCF$_3$). e.e.=100% (chiralpak AD-H 25*0.46 cm, heptane:isopropanol=9:1) (m/z)=440 (M+H)$^+$. $[\alpha]_D^{20.5}$=−197° (c=1.11, THF),

Example 4

Preparation of (−)-(cis)-N-(6,7-dicyano-8-fluoro-1,3,4,14b-tetrahydro-2H-dibenzo [b,f]pyrido[1,2-d][1,4]oxazepin-1-yl)-2,2,2-trifluoroacetamide (Formula I, R1=CF$_3$, R2=CN, R3=R4=R5=H)

A mixture of (−)-(cis)-N-(6-chloro-7-cyano-8-fluoro-1,3,4,14b-tetrahydro-2H-dibenzo[b,f]pyrido[1,2-d][1,4]oxazepin-1-yl)-2,2,2-trifluoroacetamide (7.66 g, 17.4 mmol), CuCN (3.9, 43.5 mmol), CuBr (2.5 g, 17.4 mmol) and NMP (105 mL) was stirred 20 min. at 180° C., 300 Watt with cooling in microwave (in 3 portions). After cooling down to room temperature, the reaction mixture was poured into water (1L), stirred for 10 min and the precipitate isolated. The precipitate was redissolved in ethyl acetate and the solids were removed by filtration. The clear ethyl acetate solution was washed with brine, dried (Na$_2$SO$_4$) and evaporated to dryness to give the crude compound which was purified by flash chromatography (SiO$_2$, heptane:ethyl acetate: CH$_2$Cl$_2$=7:2:1) and crystallized to give the title compound (4.09 g, 54%). $^1$H-NMR (400 MHz, DMSO) 1.68 (m, 1H), 1.82 (m, 1H), 1.84 (m, 1H), 2.04 (m, 1H), 3.47 (m, 1H), 3.87 (m, 1H), 4.37 (d, J=9.44 Hz, 1H), 4.45 (m, 1H), 7.18-7.38 (m, 4H), 7.88 (d, J=9.44 Hz, 1H), 9.25 (d, J=8.6 Hz, 1H). $^{19}$F-NMR (400 MHz, DMSO) −113.21 (Ar—F), −74.82 (COCF$_3$). e.e.=99.9% (chiralpak AS-H 25*0.46 cm, heptane: isopropanol=8:2). (m/z)=431 (M+H)$^+$. $[\alpha]_D^{20.5}$=−267° (c=1.11, THF).

Example 5

Preparation of (−)-(cis)-N-(6-chloro-7-cyano-8,12-difluoro-1,3,4,14b-tetrahydro-2H-dibenzo [b,f]pyrido[1,2-d][1,4]oxazepin-1-yl)-2,2,2-trifluoroacetamide (Formula I, R1=CF$_3$, R2=Cl, R3=R5=H, R4=F)

a. 4-bromo-5-fluoro-2-nitrophenol

To a solution of 4-bromo-3-fluorophenol (89 g, 465.9 mmol) in a mixture of CH$_2$Cl$_2$ (940 mL) and H$_2$SO$_4$ (52.1 mL, 978 mmol) at 0° C., HNO$_3$ (65%) (32.9 ml, 468 mmol) was added dropwise (the mixture turned from colourless to black). The resulting mixture was stirred at 0 °C. for 1 h and then poured into water. The organic layer was washed with brine, dried (Na$_2$SO$_4$) and the solvent was evaporated under reduced pressure to afford the crude compound which was purified by flash chromatography (SiO$_2$, heptane/toluene 1:3) to give 4-bromo-5-fluoro-2-nitrophenol (49.5 g, 45%). $^1$H-NMR (400 MHz, CDCl$_3$) 6.95 (d, J=9.0, 1H), 8.38 (d, J=6.2, 1H), 10.69 (s, 1H).

b. 2-amino-4-bromo-5-fluorophenol

A suspension of Na$_2$S$_2$O$_4$ (51.6 g, 296 mmol) in water (122 mL) was added slowly to a refluxed mixture of 4-bromo-5-fluoro-2-nitrophenol (14 g, 59.3 mmol) in ethanol (1000 mL). The resulting mixture was refluxed for 1 h. After cooling down the salts were filtered off and the filtrate was partially concentrated. Brine was added, extracted with diethyl ether, the extract dried and concentrated to give the crude title compound which was used without further purification (9.2 g, 75%). $^1$H-NMR (400 MHz, DMSO) 4.65 (br, 2H), 6.60 (d, J=11.3, 1H), 6.76 (d, J=7.8, 1H), 9.80 (br, 1H).

c. 4-bromo-2-[[(2,4-difluorophenyl)methylene]amino]-5-fluorophenol

A solution of 2-amino-4-bromo-5-fluorophenol (10.1 g, 49 mmol), 2,4-difluorobenzaldehyde (5.36 mL, 49 mmol) and p-toluenesulfonic acid (100 mg, 0.52 mmol) in toluene (250 mL) was heated to reflux in a Dean-Stark apparatus for 0.5 h and then allowed to cool to ambient temperature. After adding triethylamine (1 mL) the reaction mixture was concentrated under reduced pressure to give the crude compound which was used without further purification. (16.1 g, 99%). $^1$H-NMR (400 MHz, CDCl$_3$) 6.83 (d, J=10.2, 1H), 6.93 (m, 1H), 7.01 (m, 1H), 7.49 (d, J=7.6, 1H), 8.13 (m, 1H), 8.85 (s, 1H).

d. 8-bromo-3,7-difluorodibenz[b,f][1,4]oxazepine

To a solution of 4-bromo-2-[(2,4-difluorobenzylidene)amino]-5-fluorophenol (15 g, 45.4 mmol) in 60 mL of DMF, Cs$_2$CO$_3$ (22 g, 67.5 mmol) was added. The resulting mixture was stirred at 50° C. for 3 h and then allowed to cool to ambient temperature. Water was added and the product was collected by filtration, washed with water, and dried under reduced pressure to yield the title compound which was used without further purification (14.1 g, 100%). $^1$H-NMR (400 MHz, CDCl$_3$) 6.82-6.99 (m, 3H), 7.33 (m, 1H), 7.55 (d, J=7.8, 1H), 8.38 (s, 1H).

e. (±)-(cis)-7-bromo-8,12-difluoro-1,3,4,14b-tetrahydro-4-oxo-2H-dibenzo [b,f]pyrido[1,2-d][1,4]oxazepine-1-carboxylic acid Glutaric anhydride (7.93 g, 69.5 mmol) was added to a stirred solution of 8-bromo-3,7-difluoro-dibenz[b,f][1,4]oxazepine (14.4 g, 46.4 mmol) in xylene (30 mL) and the mixture was heated to 150° C. for 72 h. The reaction mixture was allowed to cool to ambient temperature, and diethyl ether was added. The product was collected by filtration and dried to yield the title compound which was used without further purification (16.2, 82%).

f. methyl (±)-(cis)-(7-bromo-8,12-difluoro-1,3,4,14b-tetrahydro-4-oxo-2H-dibenzo[b,f]pyrido[1,2-d][1,4]oxazepin-1-yl)carbamate To a solution of (±)-(cis)-7-bromo-8,12-difluoro-1,3,4,14b-tetrahydro-4-oxo-2H-dibenzo[b,f]pyrido[1,2-d][1,4]oxazepine-1-carboxylic acid (16.2 g, 38.2 mmol) in toluene (500 mL), triethylamine (9.7 mL, 68 mmol) and DPPA (10.6 mL, 49.1 mmol) were added. The reaction mixture was heated to reflux for 2 h. Subsequently, methanol (40 mL) was added and stirring was continued overnight at 70° C. After cooling down, the reaction mixture was washed with 0.5 M NaOH-solution (3×), dried ($Na_2SO_4$), and evaporated to afford the title compound which was used without further purification (17.3 g, 100%). (m/z)=453+455 (M+H)$^+$.

g. methyl (±)-(cis)-(7-bromo-8,12-difluoro-1,3,4, 14b-tetrahydro-2H-dibenzo [b,f]pyrido[1,2-d][1,4] oxazepin-1-yl)carbamate Borane (1.0 M in THF, 38.3 mL, 38.3 mmol) was added dropwise to a stirred solution of methyl (±)-(cis)-(7-bromo-8,12-difluoro-1,3,4,14b-tetrahydro-4-oxo-2H-dibenzo[b,f]pyrido[1,2-d][1,4]oxazepin-1-yl)carbamate (38.2 mmol) in THF (200 mL). The resulting mixture was stirred at 30° C. for 1 h. Subsequently, water was added dropwise until evolution of gas ceased. The resulting mixture was stirred for 1 h and then diluted with ethyl acetate (300 mL) and washed with brine. After drying ($Na_2SO_4$) the solvent was evaporated under reduced pressure to yield the crude title compound (16.7 g, 100%). (m/z)=439+441 (M+H)$^+$.

h. (±)-(cis)-7-bromo-8,12-difluoro-1,3,4,14b-tetrahydro-2H-dibenzo[b,f]pyrido[1,2-d][1,4]oxazepine-1-amine A mixture of acetic acid (80 mL) and hydrogen bromide (48%, 40 mL) was added to methyl (±)-(cis)-(7-bromo-8,12-difluoro-1,3,4,14b-tetrahydro-2H-dibenzo[b,f]pyrido[1,2-d][1,4]oxazepin-1-yl)carbamate (38.2 mmol), and the mixture stirred overnight at 100° C. After cooling down the reaction mixture was poured into a cold 1N NaOH solution (pH 9). It was extracted with ethyl acetate and the organic layer was washed with brine, dried ($Na_2SO_4$) and the solvent was evaporated under reduced pressure to yield the crude title compound (12.7 g, 87%) which was used without further purification. (m/z)=381+383 (M+H)$^+$.

i. (−)-(cis)-7-bromo-8,12-difluoro-1,3,4,14b-tetrahydro-2H-dibenzo[b,f]pyrido[1,2-d][1,4]oxazepine-1-amine (4S)-2-hydroxy-5,5-dimethyl-4-phenyl-1,3,2-dioxaphosphorinane 2-oxide (1:1)

To a solution of (±)-(cis)-7-bromo-8,12-difluoro-1,3,4,14b-tetrahydro-2H-dibenzo[b,f]pyrido[1,2-d][1,4]oxazepine-1-amine (12.06 g, 31.65 mmol) in 120 mL of $CH_2Cl_2$, 25 mL of 2-propanol and 25 mL of ethanol at 40° C. was added a warm solution of (+)-phencyphos (3.84 g, 15.82 mmol) in 50 mL of $CH_2Cl_2$, 25 mL of 2-propanol and 25 mL of ethanol. The mixture was heated at 40° C., $CH_2Cl_2$ was carefully evaporated until a small amount of crystals was formed, and then the mixture was gradually cooled down to ambient temperature. The precipitate was filtered off and recrystallized to yield the title compound (3.94 g, 20%).

j. (−)-(cis)-7-bromo-8,12-difluoro-1,3,4,14b-tetrahydro-2H-dibenzo[b,f]pyrido[1,2-d][1,4]oxazepine-1-amine To a solution of the phencyphos salt obtained in the previous step (3.94 g 6.32 mmol) in 150 mL of ethanol:$CH_2Cl_2$ (1:9), 1N NaOH (45 ml, 45 mmol) was added and the resulting mixture was stirred for 1 h at ambient temperature. The aqueous layer was extracted with $CH_2Cl_2$ and the combined organic layers were washed with 0.5N NaOH, dried ($Na_2SO_4$) and evaporated under reduced pressure to yield the crude title compound (2.32 g, 96%). e.e.=98.9% (chiralpak AD-H 25*0.46 cm, heptane:2-propanol=9:1).

k. (−)-(cis)-N-(7-bromo-8,12-difluoro-1,3,4,14b-tetrahydro-2H-dibenzo[b,f]pyrido[1,2-d][1,4]oxazepin-1-yl)-2,2,2-trifluoroacetamide To a solution of (−)-(cis)-7-bromo-8,12-difluoro-1,3,4,14b-tetrahydro-2H-dibenzo[b,f]pyrido[1,2-d][1,4]oxazepine-1-amine (2.32 g, 6.09 mmol) in a mixture of methanol (80 mL) and triethylamine (5.1 mL, 36.3 mmol), ethyl trifluoroacetate (4.3 mL, 36.3 mmol) was added and the resulting mixture was stirred at ambient temperature for 2 h. Water (120 mL) was added and stirred for additional 10 min. The formed precipitate was filtered off to yield the title compound (2.74 g, 94%).

l. (−)-(cis)-N-(7-cyano-8,12-difluoro-1,3,4,14b-tetrahydro-2H-dibenzo[b,f]pyrido[1,2-d][1,4]oxazepin-1-yl)-2,2,2-trifluoroacetamide A mixture of 2.74 g (5.74 mmol) of (−)-(cis)-N-(7-bromo-8,12-difluoro-1,3,4,14b-tetrahydro-2H-dibenzo[b,f]pyrido[1,2-d][1,4]oxazepin-1-yl)-2,2,2-trifluoroacetamide, CuCN (1.3 g, 14.3 mmol), CuI (0.123 g, 0.57 mmol) and NMP (25 mL) was stirred in a microwave for 20 min. at 180° C., 300 Watt with cooling. After cooling down, the reaction mixture was poured into water (500 mL). The precipitate, containing product and salts, was redissolved in ethyl acetate and the salts were filtered off. The organic layer was washed with $NH_4OH$-solution, water, and brine, dried, and concentrated to give the crude compound which was crystallized to give the title compound (1.45 g, 59%). $^1$H-NMR (400 MHz, DMSO) 1.60-1.86 (m, 3H), 2.01 (m, 1H), 3.15 (m, 1H), 3.86 (m, 1H), 4.133 (d, J=10.0, 1H), 4.35 (m, 1H), 7.00 (m, 1H), 7.03 (m, 1H), 7.44 (d, J=7.7, 1H), 7.6 (d, J=6.3, 1H), 9.23 (br-d, J=7.8, 1H). (m/z)=424 (M+H)$^+$.

m. (−)-(cis)-N-(6-chloro-7-cyano-8,12-difluoro-1,3,4,14b-tetrahydro-2H-dibenzo [b,f]pyrido[1,2-d][1,4]oxazepin-1-yl)-2,2,2-trifluoroacetamide Preparation analogous to Example 3 from (3.42 mmol) of (−)-(cis)-N-(7-cyano-8,12-difluoro-1,3,4,14b-tetrahydro-2H-dibenzo[b,f]pyrido[1,2-d][1,4]oxazepin-1-yl)-2,2,2-trifluoroacetamide, to afford the crude compound which was purified by flash chromatography ($SiO_2$, $CH_2Cl_2$/toluene 1:9) and crystallized to give (−)-(cis)-N-(6-chloro-7-cyano-8,12-difluoro-1,3,4,14b-tetrahydro-2H-dibenzo[b,f]pyrido[1,2-d][1,4]oxazepin-1-yl)-2,2,2-trifluoroacetamide (0.719 g, 46%). Mp. 174-175° C. $^1$H-NMR (400 MHz, $CDCl_3$), 1.65 (m, 1H), 1.90 (m, 2H), 2.02 (m, 1H), 2.89 (m, 1H), 3.04 (m, 1H), 2.39 (m, 1H), 4.86 (m, 1H), 6.95 (m, 3H), 7.29 (m, 1H), 7.66 (br, 1H). e.e.=100%, $R_f$=25.0 min. (chiralpak OJ-H 25*0.46 cm, heptane:ethanol=9:1). (MIM)=457. $[\alpha]_D^{20}$=−192° (c=0.885, THF)

Example 6

Preparation of (−)-(cis)-N-(6-chloro-7-cyano-8,14-difluoro-1,3,4,14b-tetrahydro-2H-dibenzo [b,f]pyrido[1,2-d][1,4]oxazepin-1-yl)acetamide (Formula I, R1=CH$_3$, R2=Cl, R3=R4=H, R5=F)

a. 4-bromo-2-[[(2,6-difluorophenyl)methylene]amino]-5-fluorophenol

Preparation analogous to Example 5, step c, from 2-amino-4-bromo-5-fluorophenol (11 g, 53.4 mmol) and 2,6-difluorobenzaldehyde (5.8 mL, 53.4 mmol) gave 4-bromo-2-[(2,6-difluorobenzylidene)amino]-5-fluorophenol (17.62 g, 100%) %). $^1$H-NMR (400 MHz, CDCl$_3$) 6.83 (d, J=10.2, 1H), 7.02 (m, 2H), 7.44 (m, 1H), 7.52 (m, 1H), 8.85 (s, 1H).

b. 8-bromo-1,7-difluorodibenz[b,f][1,4]oxazepine

Preparation analogous to Example 5, step d, from 4-bromo-2-[(2,6-difluorobenzylidene)amino]-5-fluorophenol (53.4 mmol) and Cs$_2$CO$_3$ (26 g, 80 mmol) gave the title compound (16.1 g, 97%).

c. (±)-(cis)-7-bromo-8,14-difluoro-1,3,4,14b-tetrahydro-4-oxo-2H-dibenzo [b,f]pyrido[1,2-d][1,4]oxazepine-1-carboxylic acid Preparation analogous to Example 5, step e, from 8-bromo-1,7-difluorodibenz[b,f][1,4]oxazepine (8 g, 25.8 mmol) and glutaric anhydride (5.9 g, 51.6 mmol). After cooling down, the reaction mixture was dissolved in ethyl acetate, washed with water, dried (Na$_2$SO$_4$) and evaporated to afford the title carboxylic acid (10.9 g, 100%)

d. methyl (±)-(cis)-(7-bromo-8,14-difluoro-1,3,4,14b-tetrahydro-4-oxo-2H-dibenzo [b,f]pyrido[1,2-d][1,4]oxazepin-1-yl)carbamate Preparation analogous to Example 5, step f, from (±)-(cis)-7-bromo-8,14-difluoro-1,3,4,14b-tetrahydro-4-oxo-2H-dibenzo[b,f]pyrido[1,2-d][1,4]oxazepine-1-carboxylic acid (10.94 g, 25.8 mmol), triethylamine (6.4 mL, 45.6 mmol), DPPA (7.2 mL, 33.31 mmol) and methanol (29 mL). The crude compound was purified by flash chromatography (SiO$_2$, toluene:ethyl acetate 6:4) to give methyl (±)-(cis)-(7-bromo-8,14-difluoro-1,3,4,14b-tetrahydro-4-oxo-2H-dibenzo[b,f]pyrido[1,2-][1,4]oxazepin-1-yl)carbamate (11 g, 94%).

e. methyl (±)-(cis)-(7-bromo-8,14-difluoro-1,3,4,14b-tetrahydro-2H-dibenzo [b,f]pyrido[1,2-d][1,4]oxazepin-1-yl)carbamate Preparation analogous to Example 5, step g, from methyl (±)-(cis)-(7-bromo-8,14-difluoro-1,3,4,14b-tetrahydro-4-oxo-2H-dibenzo[b,f]pyrido[1,2-d][1,4]oxazepin-1-yl)carbamate (11 g, 24 mmol), borane (1.0 M in THF, 24.2 mL, 24.2 mmol) gave the crude title compound (10.5 g, 100%).

f. (±)-(cis)-7-bromo-8,14-difluoro-1,3,4,14b-tetrahydro-2H-dibenzo[b,f]pyrido[1,2-d][1,4]oxazepine-1-amine Preparation analogous to Example 5, step h, from methyl (±)-(cis)-(7-bromo-8,14-difluoro-1,3,4,14b-tetrahydro-2H-dibenzo[b,f]pyrido[1,2-d][1,4]oxazepin-1-yl)carbamate (1.9 g, 4.3 mmol), acetic acid (9 mL) and hydrogen bromide (48%, 5 mL) gave the crude title compound (1.44 g, 88%).

g. (−)-(cis)-7-bromo-8,14-difluoro-1,3,4,14b-tetrahydro-2H-dibenzo[b,f]pyrido[1,2-d][1,4]oxazepine-1-amine (4S)-2-hydroxy-5,5-dimethyl-4-phenyl-1,3,2-dioxaphosphorinane 2-oxide (1:1)

Preparation analogous to Example 5, step i, from 2.2 g, (5.77 mmol) of (±)-(cis)-(7-bromo-8,14-difluoro-1,3,4,14b-tetrahydro-2H-dibenzo[b,f]pyrido[1,2-d][1,4]oxazepine-1-amine, 0.7 g, (2.88 mmol) of (+)-phencyphos, CH$_2$Cl$_2$ (100 mL), ethanol (5 mL) and 2-butanone (50 mL). Recrystallization gave the title compound (0.8 g, 27%).

h. (−)-(cis)-7-bromo-8,14-difluoro-1,3,4,14b-tetrahydro-2H-dibenzo[b,f]pyrido[1,2-d][1,4]oxazepine-1-amine Preparation analogous to Example 5, step j, from the phencyphos salt obtained in the previous step (1.33 g, 2.13 mmol) gave the title compound (0.8 g, 99%). e.e.=99.7% (chiralpak AD-H 25*0.46 cm, heptane:2-propanol=8:2).

i. (−)-(cis)-N-(7-bromo-8,14-difluoro-1,3,4,14b-tetrahydro-2H-dibenzo[b,f]pyrido[1,2-d][1,4]oxazepin-1-yl)acetamide To a solution of 0.4 g (1.05 mmol) (−)-(cis)-7-bromo-8,14-difluoro-1,3,4,14b-tetrahydro-2H-dibenzo[b,f]pyrido[1,2-d][1,4]oxazepine-1-amine in a mixture of CH$_2$Cl$_2$ (10 mL) and triethylamine (0.44 mL, 3.15 mmol), acetyl chloride (0.187 mL, 2.62 mmol) in CH$_2$Cl$_2$ (5 mL) was added and it was stirred at ambient temperature for 1 h. Saturated (aq) NaHCO$_3$ was added and the organic layers were washed with brine, dried (Na$_2$SO$_4$) and concentrated under reduced pressure to afford the crude compound which was used without further purification (0.44 g, 100%).

j. (−)-(cis)-N-(7-cyano-8,14-difluoro-1,3,4,14b-tetrahydro-2H-dibenzo[b,f]pyrido[1,2-d][1,4]oxazepin-1-yl)acetamide Preparation analogous to Example 5, step l, from (−)-(cis)-N-(7-bromo-8,14-difluoro-1,3,4,14b-tetrahydro-2H-dibenzo[b,f]pyrido[1,2-d][1,4]oxazepin-1-yl)acetamide (0.46 g, 1.08 mmol), CuCN (0.246 g, 2.71 mmol) and CuI (0.024 g, 0.108 mmol) gave the crude compound which was purified by flash chromatography (SiO$_2$, CH$_2$Cl$_2$:ethyl acetate) to give the title compound (−)-(cis)-N-(7-cyano-8,14-difluoro-1,3,4,14b-tetrahydro-2H-dibenzo[b,f]pyrido[1,2-][1,4]oxazepin-1-yl)acetamide (0.277 g, 69%). $^1$H-NMR (400 MHz, DMSO), 1.50 (s, 3H), 1.54-1.75 (m, 3H), 1.95 (m, 1H), 3.15 (m, 1H), 3.86 (m, 1H), 4.22 (d, J=10.6, 1H), 4.40 (M, 1H), 7.02 (m, 1H), 7.09 (d, J=8.6, 1H), 7.31 (m, 1H), 7.44 (d, J=10.2, 1H), 7.57 (d, J=7.0, 1H), 7.75 (br-d, J=9.4, 1H). $^{19}$F NMR (400 MHz, DMSO) −119, −113. (m/z)=370 (M+H)$^+$.

k. (−)-(cis)-N-(6-chloro-7-cyano-8,14-difluoro-1,3,4,14b-tetrahydro-2H-dibenzo [b,f]pyrido[1,2-d][1,4]oxazepin-1-yl)acetamide Preparation analogous to Example 3 from (−)-(cis)-N-(7-cyano-8,14-difluoro-1,3,4,14b-tetrahydro-2H-dibenzo[b,f]pyrido[1,2-d][1,4]oxazepin-1-yl)acetamide (0.277 g, 0.75 mmol) and NCS (0.10 g, 0.75 mmol). The crude compound was purified by HPLC to give the title compound (0.19 g, 62%). $^1$H-NMR (600 MHz, DMSO) 1.46-1.57 (m, 4H), 1.64 (m, 1H), 1.72 (m, 1H), 1.92 (m, 1H), 3.27 (m, 1H), 3.53 (m, 1H), 4.31 (d, J=11.6, 1H), 4.38 (m, 1H), 7.05 (m, 1H), 7.11 (d, J=8.7, 1H), 7.33 (m, 1H), 7.64 (d, J=9.8, 1H), 7.81 (br-d, J=9.8, 1H). e.e.=100%, $R_t$=17.8 min. (chiralpak OD-H 25*0.46 cm, heptane:ethanol=9:1). (MIM)=403. $[\alpha]_D^{20}$=−207° (c=1.0025, THF).

Example 7

Preparation of (−)-(cis)-N-(6-chloro-7-cyano-8,11-difluoro-1,3,4,14b-tetrahydro-2H-dibenzo[b,f]pyrido[1,2-d][1,4]oxazepin-1-yl)-2,2,2-trifluoroacetamide (Formula I, R1=CF$_3$, R2=Cl, R3=F, R4=R5=H)

a. 2-[[(5-bromo-2,4-difluorophenyl)imino]methyl]-6-fluorophenol

Preparation analogous to Example 5, step c, from 5-bromo-2,4-difluoroaniline (12.2 g, 58.57 mmol) and 3-fluoro-2-hydroxybenzaldehyde (8.2 g, 58.57 mmol) gave the title compound (19.3 g, 100%).

b. 8-bromo-4,7-difluorodibenz[b,f][1,4]oxazepine

Preparation analogous to Example 5, step d, from 2-[(5-bromo-2,4-difluorophenyl)iminomethyl]-6-fluorophenol (58.57 mmol) and Cs$_2$CO$_3$ (29 g, 89 mmol) gave the title compound (16.6 g, 91%).

c. (±)-(cis)-7-bromo-8,11-difluoro-1,3,4,14b-tetrahydro-4-oxo-2H-dibenzo [b,f]pyrido[1,2-d][1,4]oxazepine-1-carboxylic acid Preparation analogous to Example 5, step e, from 8-bromo-4,7-difluoro-dibenz[b,f][1,4]oxazepine (16.6 g, 53.54 mmol) and glutaric anhydride (9.15 g, 80.3 mmol) gave the title compound (13 g, 57%).

d. methyl (±)-(cis)-(7-bromo-8,11-difluoro-1,3,4,14b-tetrahydro-4-oxo-2H-dibenzo [b,f]pyrido[1,2-d][1,4]oxazepin-1-yl)carbamate Preparation analogous to Example 5, step f, from (±)-(cis)-7-bromo-8,11-difluoro-1,3,4,14b-tetrahydro-4-oxo-2H-dibenzo[b,f]pyrido[1,2-d][1,4]oxazepine-1-carboxylic acid (13 g, 30.66 mmol), triethylamine (7.5 mL, 53 mmol), DPPA (8.5 mL, 30.66 mmol) and methanol (32 mL) gave the crude compound (13.9 g, 100%).

e. methyl (±)-(cis)-(7-bromo-8,11-difluoro-1,3,4,14b-tetrahydro-2H-dibenzo [b,f]pyrido[1,2-d][1,4]oxazepin-1-yl)carbamate Preparation analogous to Example 5, step g, from methyl (±)-(cis)-(7-bromo-8,11-difluoro-1,3,4,14b-tetrahydro-4-oxo-2H-dibenzo[b,f]pyrido[1,2-d][1,4]oxazepin-1-yl)carbamate (30.66 mmol), borane (1.0 M in THF, 31 mL, 31 mmol) gave the crude title compound (13.4 g, 100%).

f. (±)-(cis)-7-bromo-8,11-difluoro-1,3,4,14b-tetrahydro-2H-dibenzo[b,f]pyrido[1,2-d][1,4]oxazepine-1-amine Preparation analogous to Example 5, step h, from methyl (±)-(cis)-(7-bromo-8,11-difluoro-1,3,4,14b-tetrahydro-2H-dibenzo[b,f]pyrido[1,2-d][1,4]oxazepin-1-yl)carbamate (30.66 mmol), acetic acid (50 mL) and hydrogen bromide (48%, 30 mL) gave the crude title compound (11.68, 100%).

g. (−)-(cis)-7-bromo-8,11-difluoro-1,3,4,14b-tetrahydro-2H-dibenzo[b,f]pyrido[1,2-d][1,4]oxazepine-1-amine (4S)-2-hydroxy-5,5-dimethyl-4-phenyl-1,3,2-dioxaphosphorinane 2-oxide (1:1)

Preparation analogous to Example 5, step i, from (±)-(cis)-7-bromo-8,11-difluoro-1,3,4,14b-tetrahydro-2H-dibenzo[b,f]pyrido[1,2-d][1,4]oxazepine-1-amine (30.5 mmol) and (+)-phencyphos (3.7 g, 15.29 mmol) in CH$_2$Cl$_2$ (160 mL), and ethanol (100 mL). Recrystallization gave the title compound (2.55 g, 17%).

h. (−)-(cis)-7-bromo-8,11-difluoro-1,3,4,14b-tetrahydro-2H-dibenzo[b,f]pyrido[1,2-d][1,4]oxazepine-1-amine Preparation analogous to Example 5, step j, from the phencyphos salt obtained in the previous step (2.55 g, 4.1 mmol) gave the title compound (1.51 g, 97%). e.e.=99.8% (chiralpak AD-H 25*0.46 cm, heptane:ethanol=8:2).

i. (−)-(cis)-N-(7-bromo-8,11-difluoro-1,3,4,14b-tetrahydro-2H-dibenzo[b,f]pyrido[1,2-d][1,4]oxazepin-1-yl)-2,2,2-trifluoroacetamide Preparation analogous to Example 5, step k, from (−)-(cis)-7-bromo-8,11-difluoro-1,3,4,14b-tetrahydro-2H-dibenzo[b,f]pyrido[1,2-d][1,4]oxazepine-1-amine (1.51 g, 4.0 mmol) gave the title compound (1.73 g, 91%).

k. (−)-(cis)-N-(7-cyano-8,11-difluoro-1,3,4,14b-tetrahydro-2H-dibenzo[b,f]pyrido[1,2-d][1,4]oxazepin-1-yl)-2,2,2-trifluoroacetamide Preparation analogous to Example 5, step 1, from (−)-(cis)-N-(7-bromo-8,11-difluoro-1,3,4,14b-tetrahydro-2H-dibenzo[b,f]pyrido[1,2-d][1,4]oxazepin-1-yl)-2,2,2-trifluoroacetamide (1.73 g, 3.63 mmol), CuCN (0.85 g, 9.0 mmol) and CuI (0.08 g, 0.36 mmol) gave the title compound (1.3 g, 82%).

l. (−)-(cis)-N-(6-chloro-7-cyano-8,11-difluoro-1,3,4,14b-tetrahydro-2H-dibenzo [b,f]pyrido[1,2-d][1,4]oxazepin-1-yl)-2,2,2-trifluoroacetamide Preparation analogous to Example 3 from (−)-(cis)-N-(7-cyano-8,11-difluoro-1,3,4,14b-tetrahydro-2H-dibenzo[b,f]pyrido[1,2-d][1,4]oxazepin-1-yl)-2,2,2-trifluoroacetamide (1.3 g, 3.07 mmol) and NCS (0.42 g, 3.07 mmol). The crude compound was purified by crystallization to give (−)-(cis)-N-(2H-6-chloro-7-cyano-8,11-difluoro-1,3,4,14b-tetrahydro-2H-dibenzo[b,f]pyrido[1,2-d][1,4]oxazepin-1-yl)-2,2,2-trifluoroacetamide (0.57 g, 40%). $^1$H-NMR (400 MHz, CDCl$_3$) 1.66 (m, 1H), 1.89-2.1 (m, 3H), 2.91 (m, 1H), 3.08 (m, 1H), 4.45 (m, 1H), 4.88 (m, 1H), 7.04-7.22 (m, 4H), 7.64 (br, 1H). e.e.=100%, $R_t$=22.9 min. (chiralpak OJ-H 25*0.46 cm, heptane:ethanol=9:1). (MIM)=457. $[\alpha]_D^{20}$=−196° (c=1.01, THF).

Example 8

Preparation of (−)-(cis)-N-(7-cyano-8,14-difluoro-1,3,4,14b-tetrahydro-2H-dibenzo [b,f]pyrido[1,2-d][1,4]oxazepin-1-yl)-2,2,2-trifluoroacetamide (Formula I, R1=CF₃, R2=R3=R4=H, R5=F)

a. (−)-(cis)-N-(7-bromo-8,14-difluoro-1,3,4,14b-tetrahydro-2H-dibenzo[b,f]pyrido[1,2-d][1,4]oxazepin-1-yl)-2,2,2-trifluoroacetamide Preparation analogous to Example 5, step k, from 0.408 g (1.07 mmol) of (−)-(cis)-7-bromo-8,14-difluoro-1,3,4,14b-tetrahydro-2H-dibenzo[b,f]pyrido[1,2-d][1,4]oxazepine-1-amine (Example 6, step h) gave the title compound (0.486 g, 95%).

b. (−)-(cis)-N-(7-cyano-8,14-difluoro-1,3,4,14b-tetrahydro-2H-dibenzo[b,f]pyrido[1,2-d][1,4]oxazepin-1-yl)-2,2,2-trifluoroacetamide Preparation analogous to Example 5, step 1, from (−)-(cis)-N-(7-bromo-8,14-difluoro-1,3,4,14b-tetrahydro-2H-dibenzo[b,f]pyrido[1,2-d][1,4]oxazepin-1-yl)-2,2,2-trifluoroacetamide (0.486 g, 1.01 mmol), CuCN (0.23 g, 2.57 mmol) and CuI (0.022 g, 0.1 mmol) gave the title compound (0.397 g, 92%). Mp. 262-263° C. ¹H-NMR (600 MHz, DMSO) 1.59-1.65 (m, 2H), 1.91-2.03 (m, 2H), 3.60 (m, 1H), 3.93 (d, J=14.5, 1H), 4.40 (d, J=11, 1H), 4.51 (m, 1H), 7.04 (m, 1H), 7.13 (d, J=8.7, 1H), 7.35 (m, 1H), 7.48 (d, J=10.4, 1H), 7.63 (d, J=6.4, 1H), 9.36 (br-d, J=11.0, 1H). e.e.=100%, R$_f$=16.5 min. (chiralpak AD-H 25*0.46 cm, heptane:2-propanol=9:1). (MIM)=423. [α]$_D^{20}$=−224° (c=1.08, THF).

Example 9

Preparation of (−)-(cis)-N-(6-chloro-7-cyano-8,14-difluoro-1,3,4,14b-tetrahydro-2H-dibenzo [b,f]pyrido[1,2-d][1,4]oxazepin-1-yl)-2,2,2-trifluoroacetamide (Formula I, R1=CF₃, R2=Cl, R3=R4=H, R5=F)

Preparation analogous to Example 3 from (−)-(cis)-N-(7-cyano-8,14-difluoro-1,3,4,14b-tetrahydro-2H-dibenzo[b,f]pyrido[1,2-d][1,4]oxazepin-1-yl)-2,2,2-trifluoroacetamide (0.245 g, 0.58 mmol) and NCS (0.08 g, 0.58 mmol). The crude compound was purified by HPLC to give the title compound (0.159 g, 60%). ¹H-NMR (600 MHz, CDCl₃) 1.55 (m, 1H), 1.73 (m, 1H), 1.88 (m, 1H), 2.00 (m, 1H), 3.29 (m, 1H), 3.62 (d, J=14.5, 1H), 4.47 (m, 2H), 7.06 (m, 1H), 7.16 (d, J=9.2, 1H), 2.36 (m, 1H), 7.68 (d, J=10.4, 1H), 9.39 (br, 1H). e.e.=100%, R$_f$=5.9 min. (chiralpak AD-H 25*0.46 cm, heptane:ethanol=9:1). (MIM)=457. [α]$_D^{20}$=−198° (c=1.0075, THF).

Example 10

In vivo Activity in Rat

Ovulation inhibition after oral administration of the compounds of the invention was studied in mature cyclic rats. Animals were treated with test compound (oral administration) for 1 complete cycle (4 days, from oestrus to pro-oestrus) and the number of ova in the oviduct was microscopically assessed at autopsy in the morning of the next (expected) oestrus. The average number of ova per rat was calculated; the minimal active dose (MAD) is defined as the level at which the average number of ova is reduced by 60% relative to placebo-treated animals.

As is evident from Table 1, compounds of the present invention have a much higher activity in vivo. Unexpectedly and surprisingly, the particular combination of 7-cyano and 8-fluoro substituents produces an activity profile superior to that of related compounds with only a minor difference in substitution pattern, such as compounds with a 7-cyano but without a fluorine in position 8, or with a 8-fluoro substituent but without a cyano substituent in position 7, or those which combine a cyano and a fluoro substituent in positions other than 7 and 8.

Table 1: In vivo progestagenic activity (ovulation inhibition in rat) of 7-cyano-8-fluoro compounds of the present invention and of comparable compounds with different substitution patterns.

| Example number | Structure | MAD (mg/kg) |
|---|---|---|
| example 47 of WO03/084963 | [structure] | >4 |
| eutomer of example 52 of WO03/084963 | [structure] | >4 |
| eutomer of example 54 of WO03/084963 | [structure] | >4 |
| example 57 of WO03/084963 | [structure] | >4 |

| Example number | Structure | MAD (mg/kg) |
| --- | --- | --- |
| eutomer of example 58 of WO03/084963 | 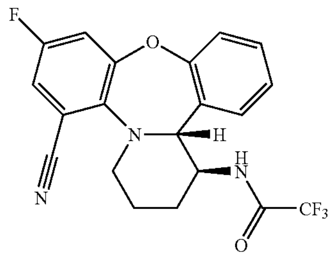 | 0.38 |
| example 59 of WO03/084963 | 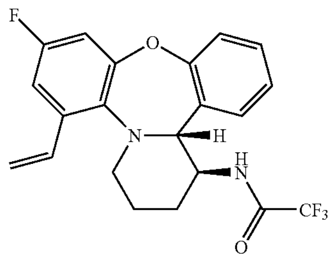 | >4 |
| example 60 of WO03/084963 | 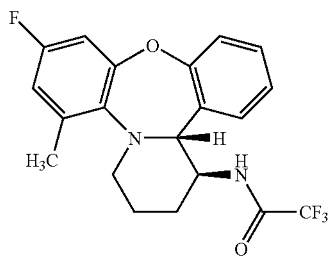 | ca 1 |
| eutomer of example 63 of WO03/084963 | 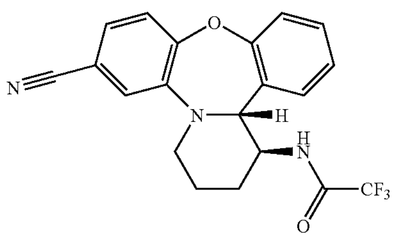 | ca 4 |
| Example 2 | 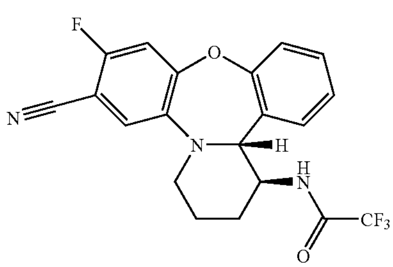 | 0.014 |
| Example 3 | 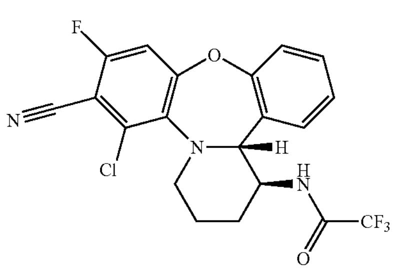 | 0.08 |

| Example number | Structure | MAD (mg/kg) |
| --- | --- | --- |
| Example 4 | 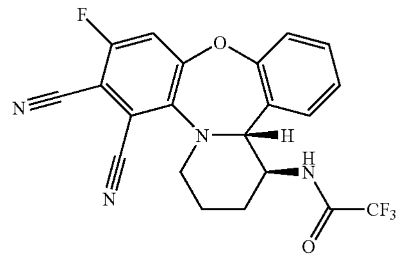 | 0.02 |
| Example 5 | 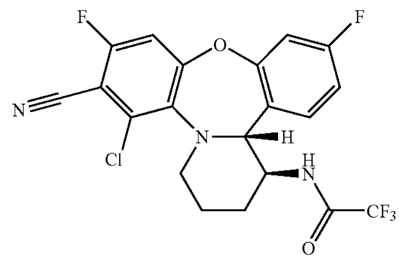 | ≦0.025 |
| Example 6 | 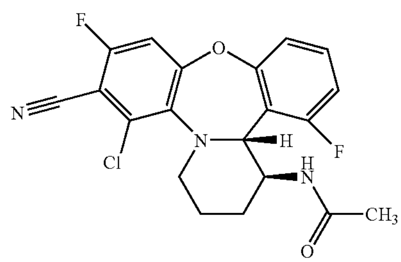 | <0.02 |
| Example 7 | 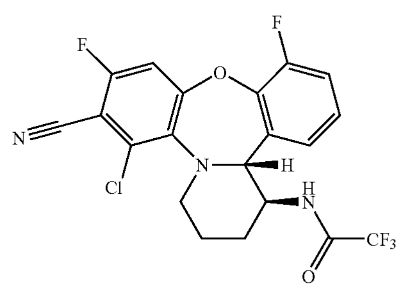 | 0.025 |
| Example 8 | 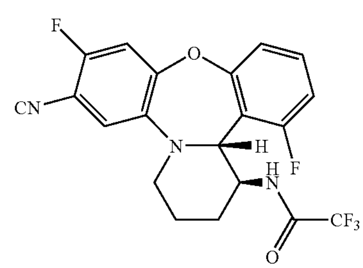 | 0.01 |

-continued

| Example number | Structure | MAD (mg/kg) |
|---|---|---|
| Example 9 | 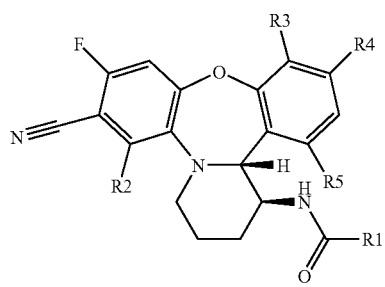 | <0.02 |

The invention claimed is:

1. A (cis)-8-fluorodibenzo[b,f]pyrido[1,2-d]oxazepine-1-amine compound according to Formula I

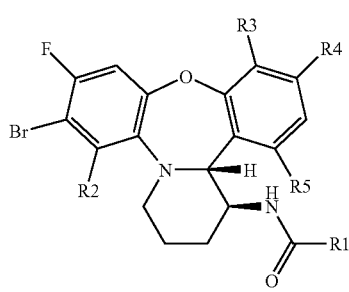

Formula I wherein
R1 is (1-4C)alkyl, optionally substituted with one or more halogen atoms; and
R2 is selected from the group consisting of H, halogen, (1-6C)alkyl, and CN; and
R3, R4, R5 each are independently H or F.

2. A compound according to claim 1, wherein R2 is H.
3. A compound according to claim 1, wherein R2 is Cl.
4. A compound according to claim 1, wherein R2 is CN.
5. A compound according to claim 1, wherein R3 is H, R4 is H and R5 is H.
6. A compound according to claim 1, wherein R3 is F and R4 and R5 are H.
7. A compound according to claim 1, wherein R4 is F and R3 and R5 are H.
8. A compound according to claim 1, wherein R5 is F and R3 and R4 are H.
9. A compound according to claim 1, wherein R1 is $CF_3$.
10. A compound according to claim 1, wherein R1 is $CH_3$.
11. A compound according to claim 1, wherein R1 is $CF_3$ and each one of R2, R3, R4 and R5 is H.
12. A compound according to claim 1, wherein R1 is $CF_3$, R2 is Cl and each one of R3, R4 and R5 is H.
13. A compound according to claim 1, wherein R1 is $CF_3$, each one of R2, R3 and R4 is H, and R5 is F.
14. A compound according to claim 1, wherein R1 is $CF_3$, R2 is Cl, both R3 and R4 are H, and R5 is F.
15. A compound according to claim 1 which is laevorotatory.
16. A pharmaceutical composition comprising a compound according to claim 1 and a pharmaceutically acceptable carrier.

17. A method of contraception comprising administering a contraceptively effective amount of a compound according to claim 1 to a subject in need thereof.
18. A method of hormone replacement therapy comprising administering a pharmaceutically effective amount of a compound according to claim 1 to a subject in need thereof.
19. A method of treating a gynaecological disorder selected from the group consisting of endometriosis, dysmenorrhea, dysfunctional uterine bleeding and severe premenstrual syndrome, the method comprising administering a pharmaceutically effective amount of a compound according to claim 1 to a subject in need thereof.
20. A (cis)-8-fluorodibenzo[b,f]pyrido[1,2-d]oxazepine-1-amine compound according to Formula II

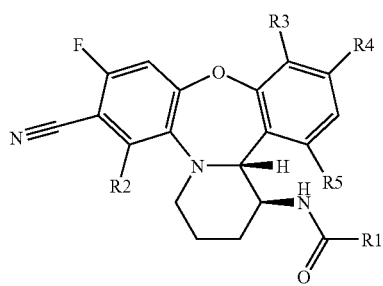

Formula II wherein R1 is (1-4C)alkyl, optionally substituted with one or more halogen atoms; and
R2 is H; and
R3, R4, R5 each are independently H or F.

21. A method of producing a compound of Formula I

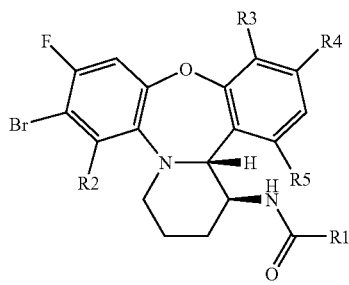

Formula I by converting a compound of Formula II by use of CuCN, optionally in the presence of CuI,

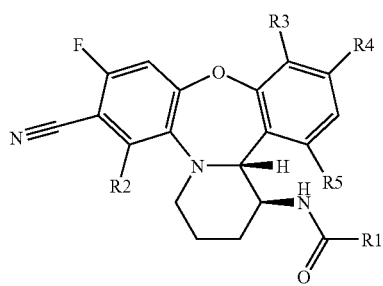

Formula II wherein R1 is (1-4C)alkyl, optionally substituted with one or more halogen atoms; and R2 is H; and R3, R4, R5 each are independently H or F, into a compound of Formula I.

22. A method of contraception comprising administering a contraceptively effective amount of a compound according to claim 11 to a subject in need thereof.

23. A method of contraception comprising administering a contraceptively effective amount of a compound according to claim 12 to a subject in need thereof.

24. A method of contraception comprising administering a contraceptively effective amount of a compound according to claim 13 to a subject in need thereof.

25. A method of contraception comprising administering a contraceptively effective amount of a compound according to claim 14 to a subject in need thereof.

26. A pharmaceutical composition comprising a compound according to claim 11 and a pharmaceutically acceptable carrier.

27. A pharmaceutical composition comprising a compound according to claim 12 and a pharmaceutically acceptable carrier.

28. A pharmaceutical composition comprising a compound according to claim 13 and a pharmaceutically acceptable carrier.

29. A pharmaceutical composition comprising a compound according to claim 14 and a pharmaceutically acceptable carrier.

30. A compound according to claim 13 which is laevorotatory.

* * * * *